US00PP24189P2

(12) United States Plant Patent
Jacobs

(10) Patent No.: US PP24,189 P2
(45) Date of Patent: Jan. 21, 2014

(54) ***LIMONIUM* PLANT NAMED 'ZALIMCLOU'**

(50) Latin Name: *Limonium hybrida*
Varietal Denomination: Zalimclou

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 83 days.

(21) Appl. No.: 13/385,873

(22) Filed: Mar. 10, 2012

(51) Int. Cl.
*A01H 5/00* (2006.01)

(52) U.S. Cl.
USPC ..... Plt./358; Plt./449

(58) Field of Classification Search
USPC ..... Plt./358, 449
See application file for complete search history.

*Primary Examiner* — Susan McCormick Ewoldt
(74) *Attorney, Agent, or Firm* — C. A. Whealy

(57) ABSTRACT

A new and distinct cultivar of *Limonium* plant named 'Zalimclou', characterized by its upright plant habit; freely flowering habit; violet blue-colored flowers arranged in compact spray-type inflorescences; and good cut flower performance.

1 Drawing Sheet

Botanical designation: *Limonium hybrida.*
Cultivar denomination: 'ZALIMCLOU'.

BACKGROUND OF THE INVENTION

The present invention relates to a new and distinct cultivar of *Limonium* plant, botanically known as *Limonium hybrida*, commercially used as a cut flower *Limonium* and hereinafter referred to by the name 'Zalimclou'.

The new *Limonium* plant is a product of a planned breeding program in Rijsenhout, The Netherlands. The objective of the breeding program is to create new cut flower *Limonium* plants with uniform plant habit and unique inflorescence shape.

The new *Limonium* plant originated from a cross-pollination conducted by the Inventor in Rijsenhout, The Netherlands in September, 2007 of a proprietary selection of *Limonium hybrida* identified as code number 05-0025-002, not patented, as the female, or seed, parent with a proprietary selection of *Limonium hybrida* identified as code number 07-Mix-001, not patented, as the male, or seed, parent. The new *Limonium* plant was discovered and selected by the Inventor as a single flowering plant from within the progeny of the stated cross-pollination grown in a controlled greenhouse environment in Rijsenhout, The Netherlands in August, 2008.

Asexual reproduction of the new *Limonium* plant since September, 2008 by tissue culture in a controlled environment in Rijsenhout, The Netherlands has shown that the unique features of this new *Limonium* plant are stable and reproduced true to type in successive generations.

SUMMARY OF THE INVENTION

Plants of the new *Limonium* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Zalimclou'.

These characteristics in combination distinguish 'Zalimclou' as a new and distinct *Limonium* plant:

1. Upright plant habit.
2. Freely flowering habit.
3. Violet blue-colored flowers arranged in compact spray-type inflorescences.
4. Good cut flower performance.

Plants of the new *Limonium* can be compared to plants of the female parent selection. Plants of the new *Limonium* differ primarily from plants of the female parent selection in leaf color as plants of the new *Limonium* have darker green-colored leaves than plants of the female parent selection. In addition, leaves of plants of the new *Limonium* are not lobed whereas leaves of plants of the female parent selection are lobed.

Plants of the new *Limonium* can be compared to plants of the male parent selection. Plants of the new *Limonium* differ primarily from plants of the male parent selection in leaf and flower color as plants of the new *Limonium* have lighter green-colored leaves and lighter violet blue-colored flowers than plants of the male parent selection.

Plants of the new *Limonium* can be compared to plants of *Limonium hybrida* 'Stastagiablue', not patented. In side-by-side comparisons conducted in Rijsenhout, The Netherlands, plants of the new *Limonium* differed primarily from plants of 'Stastagiablue' in inflorescence form as plants of 'Stastagiablue' had upright spike-type inflorescences.

BRIEF DESCRIPTION OF THE PHOTOGRAPH

The accompanying colored photograph illustrates the overall appearance of the new *Limonium* plant showing the colors as true as it is reasonably possible to obtain in colored reproductions of this type. Colors in the photograph may differ slightly from the color values cited in the detailed botanical description which accurately describe the colors of the new *Limonium* plant.

The photograph comprises a side perspective view of a typical flowering stem of 'Zalimclou'.

DETAILED BOTANICAL DESCRIPTION

The aforementioned photograph and following observations and measurements describe plants of the new *Limonium* grown during the summer in ground beds in a glass-covered greenhouse in Rijsenhout, The Netherlands and under cultural conditions typical of *Limonium* cut flower production. During the production of the plants, day temperatures ranged from 18° C. to 25° C. and night temperatures ranged from 16° C. to 18° C. Plants were pinched one time and were 20 weeks old when the photograph and description were taken. Color references are made to The Royal Horticultural Society Colour Chart, 2007 Edition, except where general terms of ordinary dictionary significance are used.

Botanical classification: *Limonium hybrida* 'Zalimclou'.

Parentage:

*Female, or seed, parent.*—Proprietary selection of *Limonium hybrida* identified as code number 05-0025-002, not patented.

*Male, or pollen, parent.*—Proprietary selection of *Limonium perezii* identified as code number 07-Mix-001, not patented.

Propagation:

*Type.*—By tissue culture.

*Time to initiate roots, summer.*—About 35 days at temperatures of 20° C.

*Time to initiate roots, winter.*—About 35 to 40 days at temperatures of 18° C. to 25° C.

*Root description.*—Fine, fibrous; white in color.

*Rooting habit.*—Moderate branching; medium density.

Plant description:

*Plant and growth habit.*—Perennial typically grown as a cut flower; plants mostly upright; basal rosette with about 30 flowering stems developing per year; freely flowering habit with numerous flowers arranged in compact spray-type panicles; moderately vigorous growth habit.

*Plant height.*—About 60 cm to 100 cm.

*Plant diameter* (*spread*).—About 30 cm to 40 cm.

*Flowering stems.*—Length: About 50 cm to 100 cm. Diameter: About 6 mm to 9 mm. Internode length: About 2 cm to 10 cm. Aspect: Erect to about 30° from vertical. Strength: Strong, rigid. Texture: Smooth, glabrous. Color: Close to 146A.

Foliage description:

*Arrangement.*—Basal rosette, simple; sessile.

*Length.*—About 25 cm to 45 cm.

*Width.*—About 8 cm to 12 cm.

*Shape.*—Obovate.

*Apex.*—Obtuse.

*Base.*—Cuneate.

*Margin.*—Entire.

*Texture, upper and lower surfaces.*—Pubescent.

*Venation pattern.*—Pinnate.

*Color.*—Developing leaves, upper and lower surfaces: Close to 137B. Fully expanded leaves, upper and lower surfaces: Close to 137A; venation, close to 145C.

Flower description:

*Flower arrangement and habit.*—Single flowers arranged in compact panicles; freely flowering habit with about 300 flowers developing per inflorescence; flowers actinomorphic and symmetrical; flowers face mostly upright.

*Fragrance.*—None detected.

*Flowering response.*—In The Netherlands, plants begin flowering about three months after planting; plants flower year round in the greenhouse.

*Post-production longevity.*—Flowers last for about three weeks; corolla not persistent, calyx persistent.

*Inflorescence height.*—About 10 cm to 25 cm.

*Inflorescence diameter.*—About 20 cm by 35 cm.

*Flower length.*—About 1 cm to 1.3 cm.

*Flower diameter.*—About 8 mm to 10 mm.

*Flower depth* (*height*).—About 4 mm to 6 mm.

*Flower buds.*—Length: About 1 cm to 1.3 cm. Diameter: About 1 mm to 3 mm. Shape: Ellipsoidal. Color: Close to N88B.

*Corolla.*—Petals per flower: Five in a single whorl, fused. Petal length: About 1.5 cm to 1.8 cm. Petal width: About 3 mm to 5 mm. Petal shape: Fusiform, roughly deltoid. Petal apex: Acute. Petal margin: Entire. Petal texture, upper and lower surfaces: Smooth, glabrous; satiny. Petal color: When opening, upper and lower surfaces: Close to N155A. Fully opened, upper and lower surfaces: Close to N155A.

*Calyx.*—Sepals per flower: Five in a single whorl, fused; calyx cup-shaped. Sepal length: About 4 mm to 6 mm. Sepal diameter: About 8 mm to 10 mm. Sepal shape: Deltoid. Sepal apex: Acute. Sepal base: Fused. Sepal margin: Entire. Sepal texture, upper and lower surfaces: Smooth, glabrous; papery. Sepal color: When opening and fully opened, upper surface: Close to N89C. When opening and fully opened, lower surface: Close to N89C.

*Peduncles.*—Length: About 1 cm to 10 cm. Diameter: About 1 mm to 2 mm. Strength: Strong. Angle: About 20 to 40° from stem axis. Texture: Smooth, glabrous. Color: Close to 137A; towards the margins, close to N137A.

*Pedicels.*—Length: About 1 mm to 3.5 mm. Diameter: About 1 mm. Strength: Strong. Angle: About 20 to 40° from peduncle axis. Texture: Smooth, glabrous. Color: Close to 137C; towards the margins, close to N137A.

*Reproductive organs.*—Androecium: Stamen number: Five per flower. Filament length: About 8 mm to 11 mm. Filament color: Close to N155A. Anther length: About 0.5 mm to 1 mm. Anther shape: Elliptical. Anther color: Close to 155B. Amount of pollen: Moderate. Pollen color: Close to 155B. Gynoecium: Pistil number: Five per flower. Pistil length: About 7 mm to 9 mm. Style length: About 6 mm to 8 mm. Style color: Close to N155A. Stigma shape: Papillate. Stigma color: Close to N155A. Ovary color: Close to 149D.

*Seeds and fruits.*—Seed and fruit development have not been observed on plants of the new *Limonium*.

Disease & pest resistance: Plants of the new *Limonium* have not been observed to be resistant to pathogens and pests common to *Limonium*.

Temperature tolerance: Plants of the new *Limonium* have been observed to tolerate temperatures ranging from about 5° C. to about 35° C.

It is claimed:

1. A new and distinct *Limonium* plant named 'Zalimclou' as illustrated and described.

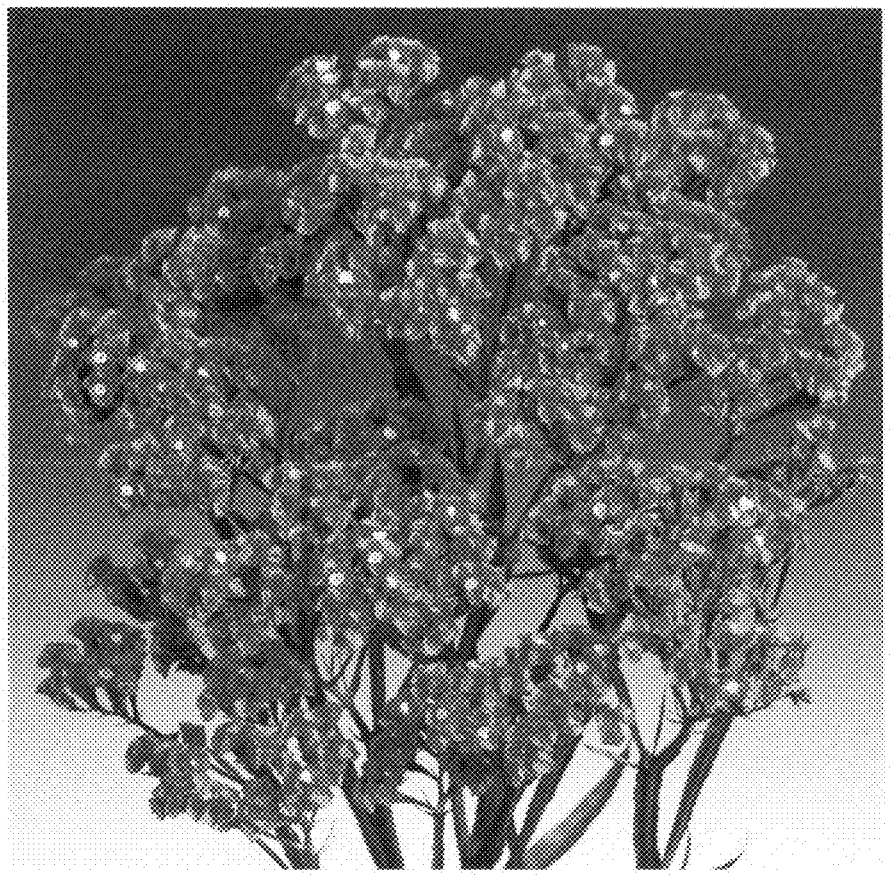

* * * * *